United States Patent [19]

Jeckel

[11] Patent Number: 5,022,855
[45] Date of Patent: Jun. 11, 1991

[54] INTRAORAL ORTHODONTIC DIRECTIONAL FORCE APPLICATOR

[76] Inventor: Norbert Jeckel, Mühlematten 21, D-7801 Umkirch, Fed. Rep. of Germany

[21] Appl. No.: 448,133

[22] Filed: Dec. 7, 1989

[30] Foreign Application Priority Data

Dec. 7, 1988 [DE] Fed. Rep. of Germany ....... 3841202

[51] Int. Cl.$^5$ .............................................. A61C 3/00
[52] U.S. Cl. ......................................... 433/18; 433/6
[58] Field of Search .......................... 433/6, 17, 18, 21

[56] References Cited

U.S. PATENT DOCUMENTS 3,092,907 6/1963 Traiger .................................. 433/18
3,293,747 12/1966 Denholtz .............................. 433/21
4,424,031 1/1984 Dahan .................................. 433/17

FOREIGN PATENT DOCUMENTS

2744740 3/1984 Fed. Rep. of Germany .......... 433/6

Primary Examiner—John J. Wilson
Attorney, Agent, or Firm—Peter K. Kontler

[57] ABSTRACT

An intraoral orthodontic applicator of directional force to molars or bucuspids in the upper or lower row of teeth has collars which can be cemented to the misoriented teeth, a substantially trough-shaped brace which overlies and conforms to the profiles of two or more anterior teeth in the respective row of teeth, and an arch wire which is separably coupled to the brace and is separably connected to the collars. The wire stores energy or is combined with resilient elements to apply a directional force which urges the brace against the adjacent anterior teeth and/or to apply a directional force which urges the collars and hence the corresponding molars or bicuspids in desired directions. The wearer can disconnect the wire from the collars and from the brace to thereupon withdraw the wire and the brace from the mouth for convenient cleaning of the corresponding row of teeth and/or of the withdrawn parts of the applicator, and the wearer can reinsert the brace and the wire without assistance from an orthodontist.

32 Claims, 3 Drawing Sheets

INTRAORAL ORTHODONTIC DIRECTIONAL FORCE APPLICATOR

BACKGROUND OF THE INVENTION

The invention relates to orthodontic apparatus in general, and more particularly to improvements in orthodontic apparatus for the application of directional force to one or more teeth of the upper or lower row of teeth in order to tip, upright or torque mal-occluded or otherwise misriented or improperly positioned teeth. Still more particularly, the invention relates to improvements in applicators of directional force to posterior mandibular or maxillar teeth.

It is often necessary to change the orientation and/or the position of certain teeth, particularly of the first or second molar at one or both sides of the upper or lower row of teeth. For example, such treatment is necessary to eliminate mal-occlusion of grinding teeth and to establish a so-called angle class I relationship. In accordance with a presently known proposal, a directional force applicator includes a substantially U-shaped inner arch which acts upon the posterior teeth and a substantially U-shaped outer arch which is affixed (e.g., welded) to the inner arch in the region of the lips. The directional force which is necessary for the so-called distalization of selected posterior teeth is supplied by an elastic cervical strap. The ends of the strap are connected to hook-shaped end portions of the outer arch. The latter transmits directional force to the inner arch the end portions of which extend into sleeves provided on collars surrounding the misoriented posterior teeth. The major part of the outer arch is located outside of the mouth and its median portion applies directional force to the immediately adjacent median portion of the inner arc. The aforementioned collars are cemented to the misoriented posterior teeth. Actual application of directional force to the sleeves (and hence to the respective collars) takes place by way of stops which are provided on the end portions of the inner arch and abut the respective sleeves when the inner arch is properly positioned in the mouth of the wearer.

When the just described conventional directional force headgear is to be put to use, the curvature of the inner and outer arches must be properly selected by the orthodontist to ensure the desired change of orientation of selected posterior teeth. Such directional force headgear is not suitable to change the orientation of different sets of teeth. Thus, if the dentition of a person requiring orthodontic treatment includes two or more pairs of misoriented teeth, such person must be furnished with two or more discrete pieces of directional force headgear. Moreover, conventional headgear can be used only to change the orientation of posterior teeth in the upper jaw because the utilization of a neck strap for arches which are to apply directional force to molars or bicuspids forming part of the lower row of teeth is likely to damage the joints between the upper and lower jaws.

Results of numerous experiments with conventional directional force headgear, including those known as hook-on headgear (such as straight pull headgear, high pull headgear and low pull cervical headgear) and those known as face bow headgear (such as modified high pull for face bow, variable pull headgear for face bow and padded cervical neck straps for face bow), indicate that the utilization of headgear results in a desirable change of orientation and/or location of selected teeth only if the applicator is used, without interruption, for not less than ten hours day after day. As a rule, orthodontists recommend to use the applicator for periods of 12-14 hours per day. Thus, the applicator must be in place while the patient is asleep as well as for several hours while the patient is awake and out of bed. This presents serious problems because many persons are incapable of falling asleep or remaining asleep while being fitted with a conventional headgear including an inner arch, an outer arch and a cervical strap or another extraoral directional force applying device. Moreover, the wearer of conventional headgear is prone to injury if the extraoral directional force applying device becomes detached from the hooks at the ends of the outer arch, irrespective of whether such detachment takes place while the wearer is awake and out of bed or while the wearer is asleep.

Another drawback of conventional headgear is that a substantial part thereof is readily visible and constitutes a cause of embarrassment to many wearers. This is a frequent cause of non use of such headgear or of use with frequent interruptions which, in turn, adversely affects the results of treatment and can render the treatment useless.

Attempts to avoid the drawbacks of aforediscussed conventional headgear with extraoral direction force applying means include the provision of intraoral directional force applicators wherein the directional force is furnished by pairs of magnets. The magnets of each pair tend to repel each other to thereby urge selected teeth in a desired direction. A drawback of such intraoral applicators is that they must remain in a wearer's mouth for extended periods of time, normally several weeks. This can affect the bone tissue and prevents the wearer from properly cleaning her or his teeth during the entire period of treatment. Still further, conventional intraoral directional force applicators are expensive because each such applicator must be individually fitted to ensure satisfactory changes of orientation and/or location of selected teeth, i.e., it is not possible to mass-produce such intraoral applicators and the wearer must visit an orthodontist whenever the applicator is to be inserted into or removed from the mouth.

OBJECTS OF THE INVENTION

An object of the invention is to provide a novel and improved intraoral orthodontic directional force applicator which is constructed and assembled in such a way that it can be readily installed in or removed from the mouth by the wearer and is more comfortable than heretofore known applicators.

Another object of the invention is to provide an intraoral applicator which can be readily cleaned by the wearer as often as desired, which can be inserted into or removed from the mouth within extremely short intervals of time, and which is simpler and less expensive than heretofore known intraoral applicators.

A further object of the invention is to provide an applicator which can be readily adjusted to serve as a means for applying directional force to selected teeth of the wearer and wherein the adjustment takes little time and can be carried out by resorting to rudimentary tools.

An additional object of the invention is to provide a simple, inexpensive and versatile directional force applicator which can be worn for extended intervals of time without embarrassment and/or discomfort.

Still another object of the invention is to provide the applicator with novel and improved means for anchoring it in the mouth of the wearer.

A further object of the invention is to provide an applicator which is less likely to adversely affect the misoriented teeth than heretofore known applicators, which can be used for the treatment of teeth in the upper or lower row of teeth, and which can be installed in the mouth of a wearer without the need for implantation of magnets or other parts.

An additional object of the invention is to provide a novel and improved method of reliably anchoring the above outlined applicator in the mouth of a wearer.

Another object of the invention is to provide an applicator which comprises or consists of a relatively small number of simple and inexpensive parts.

A further object of the invention is to provide an applicator which is hardly visible or not visible at all, irrespective of whether the wearer's mouth is open or closed.

An additional object of the invention is to provide an applicator which is less inconvenient during eating than heretofore known intraoral or part intraoral and part extraoral applicators.

SUMMARY OF THE INVENTION

The invention is embodied in an intraoral orthodontic applicator of directional force to one or more first teeth (particularly to one or more posterior teeth including the molars and bicuspids) of the upper or lower row of teeth. The improved applicator comprises at least one attachment (such as a collar) which is connectable with a first tooth (e.g., a posterior tooth including a molar of the upper or lower row of teeth), at least one brace, stay or prop (hereinafter called brace) which at least partially conforms to and serves to overlie several second teeth (particularly anterior teeth including the incisors and the canines; incisors, canines and one or more bicuspids; canines and one or more bicuspids; or incisors and one or more bicuspids) of the respective row (i.e., of the row excluding the first tooth or first teeth which is or are provided with attachments), and means for biasing the at least one attachment in a selected direction (e.g., to uplift an inclined tooth; to twist an improperly oriented tooth or to otherwise reposition a tooth). The biasing means comprises at least one first component which reacts against the at least one brace, and at least one second component which bears against the at least one attachment in the selected direction. As a rule, or at least in many instances, the directional force applicator will be furnished with two attachments for a pair of molars or bicuspids which are disposed at opposite sides of the respective row of teeth, a single brace (which can overlie at least the incisors, the incisors and the canines, or the incisors and canines and one or more bicuspids), and a biasing means including a single first component separably coupled to the brace in the region of the respective incisors or canines and two second components each of which is separably connected or connectable to a discrete attachment.

The at least one brace is preferably provided with a plate-like extension which conforms to and serves to overlie the upper or lower jaw at the lingual side of the respective row of teeth. Such brace can be made of, or can at least contain, a plastic material and can be produced by deep-drawing. It is preferred to make the brace of a light-transmitting, most preferably transparent, plastic material. It is also possible to employ a brace having a plastic carrier and connectors which are supported by the carrier and serve to engage several second (preferably anterior) teeth of the respective row of teeth, i.e., of that row which includes one or more posterior teeth with attachments affixed thereto. Each attachment can include a collar which surrounds and can be glued to a first tooth, such as a molar or a bicuspid.

The biasing means preferably further comprises means for separably connecting the at least one attachment to the at least one second component of the biasing means. Such connecting means can include a female element (e.g., a sleeve or tube) and a male element which is receivable in the female element. One of these elements is provided on the at least one attachment, and the other element is provided on or forms part of or constitutes the at least one second component of the biasing means. For example, the sleeve can be secured to the at least one attachment to extend in substantial parallelism with the adjacent teeth of the respective row of teeth when the at least one attachment is properly affixed to a first tooth of such row, and the male element of the connecting means can include a plug, pin, stud or a like part which is provided on or constitutes the at least one second component and can be inserted into or extracted from the sleeve. The connecting means is preferably disposed at the level, or at the cranial side, of the coupling means between the first component of the biasing means and the brace so that the biasing means can urge the brace against the at least two second teeth of the upper or lower row of teeth.

The coupling means can include a wire which constitutes or forms part of the first component of the biasing means, and a socket which is provided in the at least one brace and removably receives the wire (the brace can retain the wire by snap action). The socket is or can be located in the region of the incisors and/or canines when the brace overlies two or more anterior teeth of the upper or lower row of teeth.

The aforementioned connecting means can further comprise at least one resilient element which is interposed between the male and female elements of the connecting means. The resilient element can include one or more coil springs, one or more tubes made of an elastomeric material, a combination of two or more different springs and/or tubes, or any other resilient element which can urge the at least one attachment in the selected direction when the male element is properly introduced into the female element. The connecting means can further comprise a stop which is provided on the male element and serves as a retainer for the resilient element, i.e., the resilient element can react against the stop to bear against the female element which, as stated above, can be affixed to or formed as an integral part of the at least one attachment. As a rule, the male element of the connecting means is elongated (it can include or constitute a length of wire), and the stop is preferably movable longitudinally of the male element. The connecting means then further comprises a screw or any other suitable means for separably affixing the stop to a selected portion of the male element; this renders it possible to select the force with which the at least one attachment is urged in the selected direction.

The biasing means can further comprise at least one resilient component which operates between the first and second components to bias the second component toward the root of the first tooth to which the at least one attachment is connected and/or to bias the first component (and hence the at least one brace) toward the roots of the second teeth which are overlapped by the brace, i.e., to urge the brace gingivally when the applicator is properly installed in the mouth to apply a directional force to one or more posterior teeth of the upper or lower row of teeth.

The biasing means can comprise a springy wire (e.g., a length of steel wire) including a first portion forming part of or constituting the first component, a second portion forming part of or constituting the at least one second component, and a third portion forming part of or constituting the aforementioned resilient component and being disposed between the first and second portions. The third portion can include one or more convolutions and is stressed when the applicator is properly installed in the mouth of a wearer. The wire can be a U-shaped or C-shaped arch wire including a web constituting the aforementioned first portion and two legs constituting the second portions. The aforementioned coupling means can constitute a detent which establishes a separable snap-in connection between the brace and the web of the U- or C-shaped wire. The web is or can constitute a substantially straight length of wire which is receivable by snap action in a complementary elongated socket at the lingual side of the brace, preferably in the region of the incisors or canines. Means can be provided to hold the wire of the first component of the biasing means against longitudinal movement in the socket; such holding means can include shoulders which flank the socket and abut or are immediately adjacent portions of the brace to thus maintain the wire in an optimum position in the longitudinal direction of the socket.

If the biasing means includes a U-shaped or C-shaped arch wire having a web forming part of or constituting the first component and two legs one of which forms part of or constitutes the at least second component, the one leg includes a tip or free end portion which constitutes the aforementioned male element of the connecting means and extends into the sleeve-like female element on the at least one attachment. The aforesaid resilient element then reacts against the tip of the one leg and bears upon the female element to apply thereto a force in the selected direction, e.g., in a direction to move the first tooth which carries the at least one attachment away from the immediately adjacent (anterior) tooth. As mentioned above, the resilient element can include an elastic tube or a coil spring which surrounds the tip of the one leg to react against a preferably adjustable stop on the one leg and to bear against the sleeve-like female element of the connecting means.

The exposed surface of the brace can conform to the profiles of the adjacent row of teeth confronting the row including the first tooth and the second teeth. Thus, if the brace overlies the incisors and canines of the upper row of teeth, its exposed surface is or can be configurated to follow the outlines of incisors and canines of the lower row of teeth.

If the applicator is used to apply directional force to a mesially inclined molar forming part of the lower (mandibular) row of teeth and being separated from the nearest anterior tooth (e.g., another molar or the rearmost bicuspid) by a gap, the aforementioned resilient component of the biasing means can be designed to apply to the at least one attachment a force in a direction to upright the inclined molar. The biasing means of such attachment can further comprise the aforementioned resilient element which acts in the longitudinal direction of the piece of wire forming part of or constituting the one leg of the U- or C-shaped arch wire. Thus, the resilient component of the biasing means can assist the resilient element or elements of the connecting means to apply directional force against the inclined molar.

The novel features which are considered as characteristic of the invention are set forth in particular in the appended claims. The improved applicator itself, however, both as to its construction and the mode of installing the same, together with additional features and advantages thereof, will be best understood upon perusal of the following detailed description of certain presently preferred specific embodiments with reference to the accompanying drawing.

DESCRIPTION OF PREFERRED EMBODIMENTS

Figure 1:
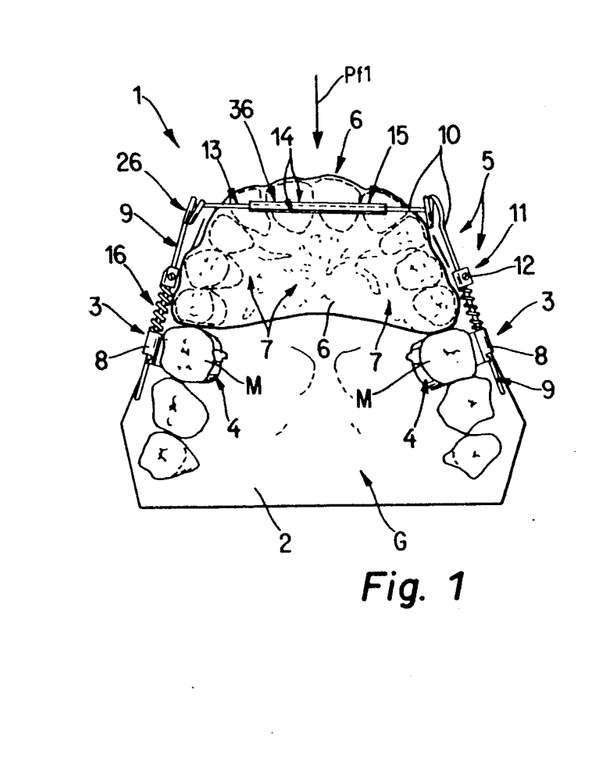
FIG. 1 is a bottom plan view of a model of the upper jaw and of an intraoral directional force applicator which embodies one form of the present invention and is shown in the operative position in which its attachments are cemented to the foremost molars at both sides of the upper row of teeth.
Figure 2:
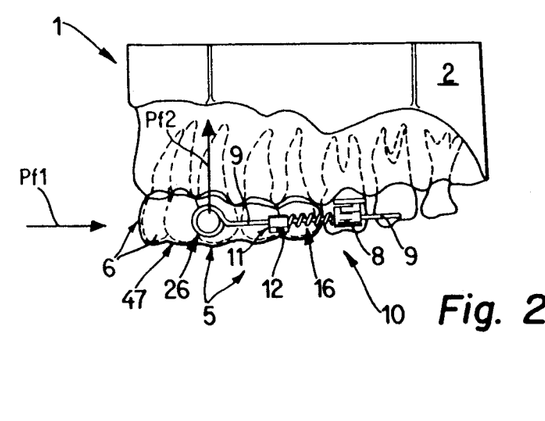
FIG. 2 is a side elevational view of the model as seen from the right-hand side of FIG. 1.
Figure 3:
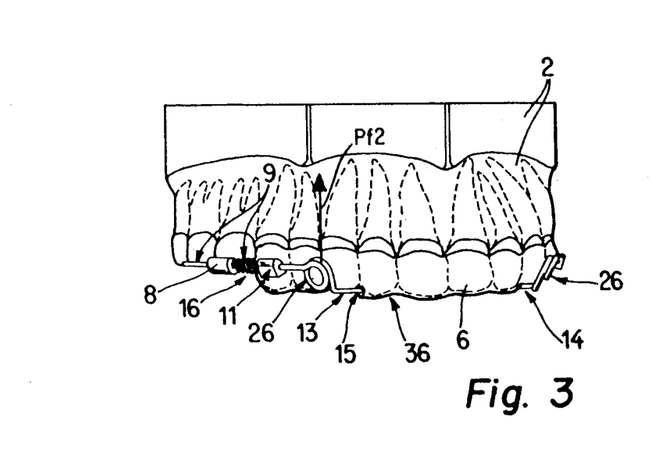
FIG. 3 is a front right-hand perspective view of the model of FIGS. 1 and 2.

FIGS. 1 to 3 show an intraoral orthodontic directional force applicator 1 which is mounted on a model 2 of the upper jaw. The purpose of the applicator 1 is to distalize and/or otherwise change the position and/or orientation of one or more posterior teeth such as the two foremost molars M (dens molares I). The same applicator can be used (possibly with some minor changes) to change the position and/or orientation of other molars or the position and/or orientation of one or more bicuspids. The need for treatment involving the use of the applicator 1 will arise, for example, when the orthodontist recommends to change the position of posterior teeth which are mal-occluded. Though FIGS. 1 to 3 show the applicator 1 in proper position with reference to the upper row of teeth, an analogous applicator can be used with equal advantage to tip, uplift, torque and/or otherwise change the position and/or orientation of one or more posterior teeth forming part of the lower row of teeth. The illustrated applicator 1 is set up to apply to the foremost molars M a force in the direction of arrow Pf1, i.e., away from the rearmost bicuspids.

With the exception of the row of teeth, the model 2 is or can be made of light-transmitting (e.g., transparent) plastic material. The applicator 1 includes two attachments 4 in the form of narrow collars or bands which are applied around and are or can be cemented to the misoriented molars M. The applicator 1 further comprises a brace, stay or prop 6 (hereinafter called brace) which is preferably made of a plastic material (e.g., a transparent or translucent plastic material) and conforms to and overlies the anterior teeth (namely all teeth, including the incisors, the canines and the bicuspids, in front of the foremost molars M) of the illustrated row of teeth, and a biasing device 5 including an arch wire 10 with a first component or web 13 reacting against the bridge 6 and two second components or legs 9 bearing against the attachments 4 to apply to the molars M a force in the direction of the arrow Pf1. Still further, the applicator 1 comprises two connecting units 3 which serve to separably connect the legs 9 with the respective attachments 4, and a detent means or coupling 36 which separably secures the web 13 to the bridge 6 in the region of the incisors and canines of the illustrated row of teeth. As mentioned above, the improved applicator 1 need not be used solely for changing the orientation of one of the illustrated molars M (dens molares I) but can be used with equal or similar advantage to change the orientation or position of certain other molars and/or bicuspids, for example, two dens molares II, dens praemolares I or dens praemolares II.

The collars which constitute or form part of the attachments 4 are individually applied around and are cemented to the selected posterior teeth (molars or bicuspids) by an orthodontist and remain in place for the duration of treatment. The inner sides of the attachments 4 closely follow the outlines of the respective molars M. The connecting units 3 enable the wearer or an orthodontist to rapidly detach the biasing device 5 from the molars M as soon as the coupling 36 is disengaged, and this renders it possible to remove the biasing device 5 and the brace 6 from the mouth for the purposes of cleaning and/or inspection as well as to facilitate thorough cleaning of the row of teeth including the molars M and the attachments 4 thereon. The illustrated attachments 4 (each of which includes a collar or band surrounding the respective molar M) can be omitted if certain portions of the connecting units 3 are directly affixed to the molars M; such portions of the connecting units 3 then constitute attachments which can apply a directional force to the molars M. For example, certain portions of the connecting units 3 can be bonded to the enamel of the molars M by resorting to a suitable plastic adhesive.

The biasing device 5 cooperates with the brace 6 (this brace can be said to resemble an arcuate trough) to furnish the required distalizing force acting in the direction of arrow Pf1. If the applicator 1 is worn each day for the prescribed intervals of time (e.g., 14 hours per day), continuous application of distalizing force in the direction of arrow Pf1 results in displacement or shifting of the molars M in directions away from the adjacent bicuspids and away from the adjacent rearmost portion of the brace 6. The latter need not necessarily follow the outlines of all teeth in front of the molars M, as long as it can be reliably held in engagement with two or more teeth preferably including some or all of the incisors, one or both canines and one or more bicuspids. In the embodiment which is shown in FIGS. 1 to 3, the direction (arrow Pf1) of the force acting upon the molars M is selected in such a way that the biasing device 5 tends to move the attachments 4 away from the brace 6 and vice versa. In order to reduce the likelihood of tilting and/or any other undesirable displacement of the brace 6 relative to the anterior teeth which are overlapped thereby and relative to the molars M, this brace preferably comprises a substantially plate-like and preferably large extension 7 at the lingual side of the illustrated row of teeth. The extension 7 is preferably configured to follow the outline of the adjacent portion of the palate G. In spite of such reliable mounting of the brace 6 in the mouth of the wearer, it can be rapidly and effortlessly removed from the mouth as soon as the coupling 36 is disengaged so that the biasing device 5 can be extracted ahead of the brace. As will be fully described hereinafter, the legs 9 of the biasing device 5 can be separated or disconnected from the attachments 4 as soon as the coupling 36 is disengaged, and such disconnection merely involves a movement of the biasing device 5 counter to the direction which is indicated by the arrow Pf1. There is no need to positively secure the brace 6 to the upper jaw, e.g., by means of numerous bands or in any other manner which invariably necessitates the presence of an orthodontist. Thus, the wearer can remove and reinstall the applicator 1 whenever necessary, for example, after a prolonged interval of continuous use and preparatory to cleaning of the teeth and/or preparatory to cleaning of the removed parts 5, 6 of the applicator.

The brace 6 (including its plate-like extension 7) preferably constitutes a one-piece body which is made of suitable (transparent or translucent) plastic material and which can be produced by deep-drawing or in accordance with any other suitable technique. This contributes to lower cost of the brace 6 and of the entire applicator 1. The illustrated brace 6 is stable and can cooperate with the biasing device 5 to produce the required directional force. For example, 8 ounces of force is often considered adequate during the first week of use, and the force is thereafter increased to 16 ounces at each side.

Each connecting unit 3 comprises a female element 8 in the form of a sleeve or tube extending in the longitudinal direction of the adjacent teeth of the upper row of teeth at the buccal side of the respective molar M and being fixedly or otherwise secured to the corresponding attachment 4, and an elongated stud- or pin-shaped male element constituting the rear end portion of the respective leg 9. The arch wire 10 of the biasing device 5 is substantially C- or U-shaped (see particularly FIG. 1) and is preferably dimensioned in such a way that only the end portions of the web 13 and the legs 9 are located at the labial or buccal side of the illustrated row of teeth. The wire 10 can be made of stainless steel or an equivalent material with a diameter of 0.8 to 2 mm, preferably 1 to 1.3 mm.

Each connecting unit 3 further comprises a stop 11 which is preferably movable longitudinally of the rear end portion (male connecting element) of the respective leg 9 and can be affixed to the leg in a selected position by a screw 12 or in any other suitable way. This enables a resilient element 16 (such as a coil spring or a tube made of elastomeric material) to react against the stop 11 and to bear against the adjacent end of the sleeve 8 in order to urge the respective attachment 4 in the direction of arrow Pf1. The position of the stop 11 relative to the respective leg 9 can be altered in order to increase or reduce the bias of the resilient element 16 which surrounds the respective leg 9 in the region between the stop 11 and the adjacent sleeve 8. Each stop 11 can constitute a simple annulus which can be readily shifted to any desired position along the corresponding leg 9 as soon as the screw 12 is loosened or removed.

The aforementioned coupling 36 between the biasing device 5 and the brace 6 includes the straight central portion of the web 13 and the adjacent portion of the brace, namely a portion which defines an elongated socket 14 communicating with a relatively narrow slot 15 in order to ensure that the web 13 must be forced into the socket and is then received in and held by the brace 6 by snap action. The entire web 13 is preferably straight, the same as the socket 14 in the lingual side of the brace 6, i.e., in that side which faces away from the palate G. The illustrated socket 14 is located beneath the first and second incisors (dens incisivus I and II) and immediately in front of the canines (dens caninus). In order to enhance the reliability of the applicator 1, and more specifically the stability of the coupling 36 between the biasing device 5 and the brace 6, at least the diameter of that portion of the length of wire which constitutes the web 13 can exceed the diameters of the wires constituting the legs 9. For example, the diameter of the web 13 can equal or approximate 1.8 mm if the diameter of a leg 9 is 1 to 1.3 mm. The diameter of the surface bounding the major portion of the socket 14 can equal or only slightly exceed the diameter of the web 13 but the width of the slot 15 leading to the socket 14 is less than the diameter of the web 13 so that the latter must be forced into the socket and this entails temporary deformation of plastic material around the slot 15. Nevertheless, the wearer or an orthodontist can readily extract the web 13 from the socket 14 by exerting a moderate force in a direction to move the web 13 toward and through the slot 15.

The positions of the stops 11 with reference to the legs 9 of the biasing device 5 determine the magnitude of forces which are applied to the respective sleeves 8 and hence to the corresponding attachments 4 in the direction of arrow Pf1, i.e., in a direction to move the molars M rearwardly and away from the adjacent second bicuspids. If the positions of the stops 11 with reference to the respective legs 9 are or should remain fixed, the magnitude of force acting in the direction of arrow Pf1 can be changed by replacing the illustrated resilient elements 16 with stronger or weaker resilient elements. As mentioned above, the illustrated coil springs 16 constitute but one form of resilient elements which can be used to react against (the stops 11 on) the legs 9 and to bear upon the sleeves 8 in a selected direction. These coil springs can be replaced by or used jointly with tubes consisting of or containing an elastomeric material. Still further, it is possible to mount a first magnet on each sleeve 8 and to mount a second magnet on each leg 9; the first magnets tend to repel the respective second magnets to thereby generate the required directional force.

The resilient elements 16 or their equivalents can constitute the only means for actually generating a directional force when the units 3 are operative to connect the legs 9 with the respective attachments 4 while the coupling 36 is engaged. However, it is equally within the purview of the invention to employ the resilient elements 16 jointly with or to replace these resilient elements with other resilient means, e.g., with resilient components shown at 26 and constituting convoluted portions of the arch wire 10 in regions between the ends of the web 13 and the front end portions of the legs 9. The wire of the biasing device 5 is made of a springy material and the resilient components 26 (each of which can consist of one or more convolutions) are stressed when the coupling 36 is engaged and the rear end portions of the legs 9 extend into the respective sleeves 8. An advantage of the resilient components 26 is that they form integral parts of the arch wire 10, i.e., they can be formed at the time the arch wire is produced, and that such simple resilient components can be readily cleaned. Moreover, the resilient components 26 cannot be lost or misplaced because they are integral parts of the relatively large arch wire 10. In addition, the resilient components 26 can be readily designed to apply a force having a component in the cranial direction (arrow Pf2 in FIG. 2), i.e., toward the cranium above the upper jaw. Such force even further reduces the likelihood of accidental shifting of the brace 6 relative to the upper row of teeth and/or relative to the palate G when the coupling 36 is engaged and the rear end portions of the legs 9 extend into the respective sleeves 8. As mentioned above, the resilient components 26 can be used jointly with (as shown) or in lieu of the resilient elements 16. If they are used alone, the resilient components 26 must produce the required directional force (arrow Pf1) as well as (if necessary and/or desired) the required force in the direction of arrow Pf2. An advantage of the resilient components 26 is their simplicity and low cost as well as the convenience of cleaning and making. On the other hand, the resilient elements 16 (or their equivalents, such as the aforediscussed pairs of magnets and/or elastic tubes) exhibit the advantage that they permit rapid and accurate adjustment of the magnitude of directional force.

The level of the coupling 36 with reference to the level of the sleeves 8 is preferably selected in such a way that, when the rear end portions of the legs 9 are properly received in the corresponding sleeves 8, the arch wire 10 does not exhibit a tendency to move the brace 6 away from the adjacent anterior teeth, i.e., the platelike extension 7 of the brace 6 does not tend to move away from the adjacent portion of the palate G. On the contrary, the resilient elements 16 and/or the resilient components 26 preferably apply a force (arrow Pf2) in a direction toward the cranium to urge the brace against the adjacent anterior teeth and to thus maintain the extension 7 in immediate proximity to the palate G.

In order to install the applicator 1 in the mouth, the wearer or an orthodontist inserts the brace 6 in a first step prior to insertion of the biasing device 5. The latter is inserted in such a way that the rear end portions of the legs 9 are introduced into the respective sleeves 8 and are pushed inwardly to stress the respective resilient elements 16 until the web 13 is adjacent the slot 15. The last step involves forcing the web 13 through the slot 15 and into the socket 14 at the lingual side of the brace 6. This results in requisite stressing of the resilient components 26 which then generate the desired force in the direction of arrow Pf1 and/or Pf2. The resilient elements 16 are slipped onto the respective legs 9 behind the stops 11 prior to insertion of the arch wire 10 into the mouth. As mentioned above, the attachments 4 or their equivalents (such as the sleeves 8 of the connecting units 3) are cemented to the molars M by an orthodontist and remain in place for the duration of treatment. The positions of stops 11 relative to the respective legs 9 will be selected by the orthodontist who will shift the stops in order to increase the bias of the respective resilient elements 16 after the attachment 1 has been put to use for a certain number of days. As stated above, the stops 11 can be more or less permanently affixed to the respective legs 9 if the orthodontist selects to change the magnitude of force acting in the direction of arrow Pf1 by replacing the illustrated resilient elements 16 with stronger or weaker resilient elements. In order to reduce the likelihood of losing or misplacing the resilient elements 16 or their equivalents when the applicator 1 is not in use, the front end portions of these resilient elements can be bonded to the respective stops 11. The bonds are preferably of such nature that the resilient elements 16 can be readily separated from the respective stops 11 when necessary, e.g., to replace a resilient element which is incapable of applying a requisite directional force due to aging or for any other reason. The manipulation of applicator 1 is simplified if the resilient elements 16 are bonded or otherwise secured to the respective stops 11 because the person in charge of inserting the arch wire 10 need not inspect the legs 9 for the presence or absence of resilient elements 16 but merely concentrates on the task of introducing the rear end portions of the legs 9 into the respective sleeves 8 prior to snapping the web 13 into the socket 14.

The problem of misplacing or losing the resilient components 26 does not arise at all because these components are integral parts of the arch wire 10, i.e., of the biasing device 5. The orthodontist can shape the arch wire 10 in order to increase or reduce the bias of the resilient components 26, for example, to ensure that the component of force acting in the cranial direction (arrow Pf2) will suffice to prevent any undesired shifting of the brace 6 relative to the adjacent teeth and the palate G.

An important advantage of the improved applicator 1 is its simplicity and compactness. Compactness is of great importance to many wearers of directional force applicators because this ensures that the inserted applicator is fully concealed or is hardly visible even while the wearer's mouth is open or not entirely closed. This, in turn, increases the likelihood that even a self-conscious wearer will use the applicator for prescribed intervals of time so that the treatment is much more likely to be successful than treatments involving the use of heretofore known applicators.

The socket 14 and the slot 15 can be formed in the following way: A tubular or solid rod-like insert is placed in proper position corresponding to that in front of the canines prior to the deep-drawing step and is removed from the freshly formed brace when such step is completed. The insert is removed in the axial direction and a slot 15 of requisite width is formed in a next-following step, e.g., by resorting to a circular milling tool or another suitable tool which is moved longitudinally of the socket 14. Alternatively, the insert can constitute a tube which remains embedded in the brace 6 so that it surrounds the socket 14. The slot 15 is obtained by removing material from the embedded tubular insert so that the web 13 of the arch wire 10 can be forced into or extracted from the interior of the insert.

A further important advantage of the improved applicator is that its brace 6 need not be secured to the teeth by bands or in any other permanent and time-consuming manner. This enables the wearer to rapidly insert or remove the brace 6 and the arch wire 10 without any assistance from the orthodontist.

Still another advantage of the improved applicator is that it ensures desirable changes of orientation and/or position of those teeth which are in need of such adjustment but does not appreciably affect the positions of teeth which are overlapped by and separably connected with the brace.

A further advantage of the applicator is that it is highly unlikely to cause decaying of those teeth which are in contact with the brace 6. The reason is that such teeth need not be bonded to the brace and that they are not contacted by the biasing device 5.

Since the entire applicator is fully accommodated in the mouth of the wearer, such person need not carry a strap and/or any other type of extraoral gear which is highly desirable since a neck strap is likely to affect cervical muscles and the upper part of the vertebra. The absence of any need for external gear is further desirable in that it reduces the likelihood of injury to the wearer, either intentional (e.g., by a juvenile) or accidentally. Moreover, the applicator can be utilized for distalization of posterior teeth in the upper as well as in the lower row of teeth because it does not affect the joints between the upper and lower jaws.

If the teeth which require a change of orientation are molars, the brace 6 can overlie a large number of teeth in front of the molars, for example (and as actually shown in FIGS. 1-3) a total of ten anterior teeth. This ensures the distribution of reaction forces among a substantial number of teeth which, in turn, greatly reduces the likelihood of changes of orientation of these teeth, i.e., changes of orientation are limited to those teeth which carry collars 4 or other types of attachments.

If desired, one or more parts of a composite biasing device can be integrated into the brace 6 during deep-drawing. This contributes to lower cost and ensures highly accurate positioning of such parts relative to the brace. The latter preferably is, but need not always be, made of a single piece of plastic material.

Certain presently preferred types of collars which constitute or form part of attachments 4 are disclosed, for example, in German Pat. No. 27 44 740. Such attachments ensure predictable application of directional forces. However, and as already mentioned above, it is possible to employ other types of attachments, e.g., adhesive materials which serve to bond the sleeves 8 of the connecting units 3 directly to the misoriented or misplaced posterior teeth.

Figures 4, 5, 6, 7:
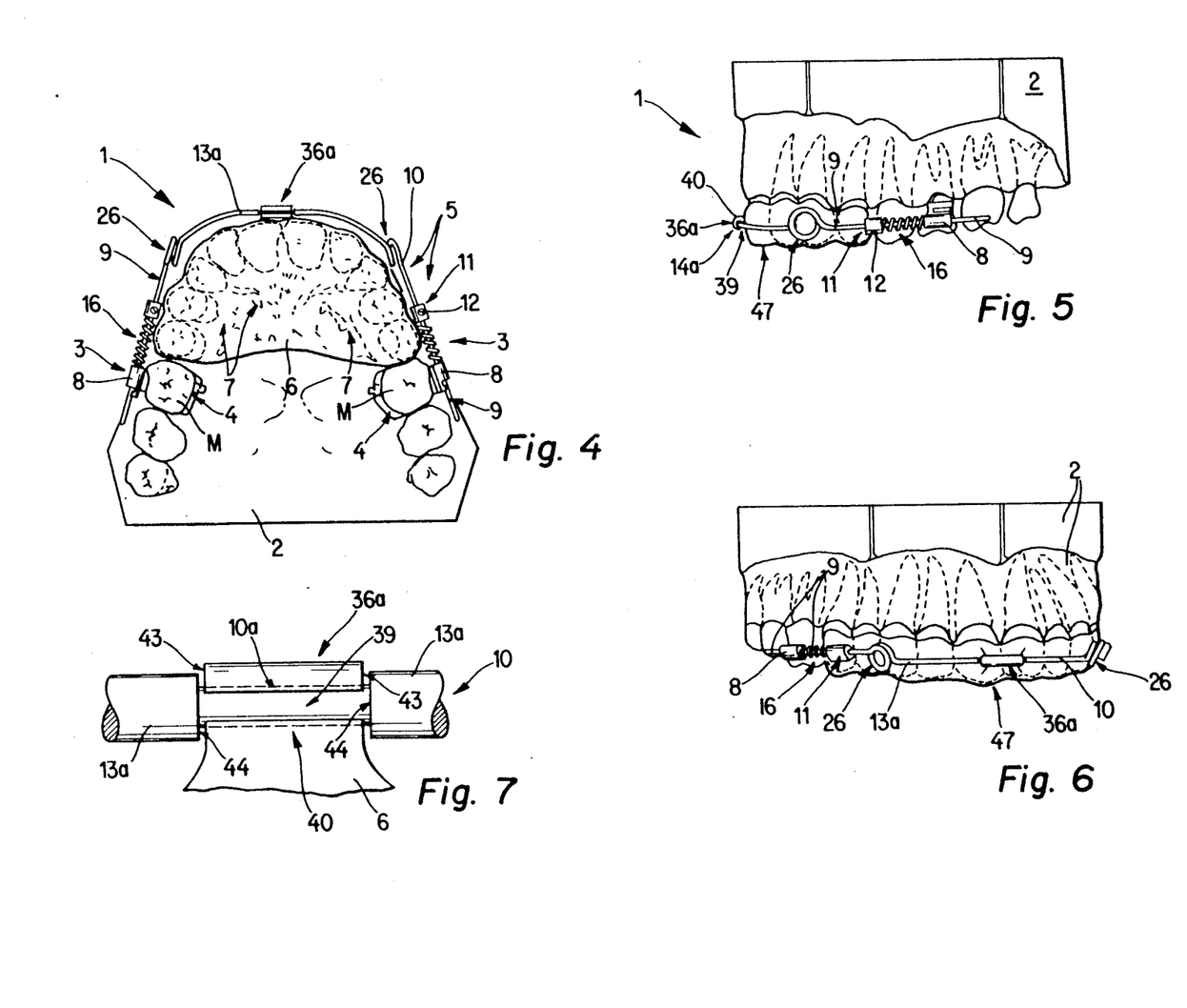
FIG. 4 is a bottom plan view of a model of the upper jaw and of a modified directional force applicator wherein the first component of the biasing means is separably coupled to the front side of the brace.
FIG. 5 is a side elevational view as seen from the right-hand side of FIG. 4.
FIG. 6 is a front right-hand perspective view of the model which is shown in FIGS. 4 and 5.
FIG. 7 is an enlarged view of a detail in the applicator of FIGS. 4 to 6, showing the means for holding the biasing means against sidewise movement with reference to the upper row of teeth.

FIGS. 4 to 6 show a slightly modified applicator 1. The main difference between the applicators of FIGS. 1-3 and 4-6 is that the coupling 36a of the applicator of FIGS. 4-6 is located at the labial side of the incisors which are overlapped by the brace 6. Moreover, the straight or substantially straight web 13 of the arch wire 10 of FIGS. 1 to 3 is replaced with an arcuate web 13a the median portion of which is releasably held in the socket 14a of the coupling 36a. The female part of the coupling 36a (i.e., the part which is rigid or integral with the brace 6 in front of the incisors) resembles a hook which can yield during insertion or extraction of the median portion 10a (FIG. 7) of the arcuate web 13a. The slot 39 leading to the socket 14a of the coupling 36a confronts the (non-illustrated) lower jaw of the wearer, i.e., the median portion 10a of the web 13a is coupled to the brace 6 by moving such median portion upwardly toward the cranium.

The details of a presently preferred front coupling 36a are shown in FIG. 7. The median portion 10a of the web 13a has a diameter slightly exceeding the width of the slot 39 leading to the socket 14a for the portion 10a. The web 13a has two shoulders 44 which flank the slot 39 and the socket 14a and cooperate with adjacent shoulders 43 of the neighboring portion 40 of the brace 6 to hold the web 13a (and hence the entire arch wire 10) against any movement in the longitudinal direction of the median portion 10a and slot 39. The portion 40 projects slightly forwardly beyond the major part of the brace 6. The force with which the median portion 10a of the web 13a is retained in the socket 14a of the coupling 36 should suffice to ensure that the resilient components 26 can urge the brace 6 upwardly (as indicated by the arrow Pf2 in FIGS. 2 and 3) in order to reduce the likelihood of downward movement of the brace 6 but without expelling the median portion 10a from the socket 14a of the coupling 36a.

An advantage of the applicator 1 of FIGS. 4 to 6, preferably with a coupling 36a of the type shown in FIG. 7, is that the wearer can more readily locate the coupling 36a in order to force the median portion 10a of the arcuate web 13a into or to expel such median portion 10a from the socket 14a. Moreover, a larger portion of the arch wire 10 is accessible to the hand of the wearer or to the hand of an orthodontist.

An advantage of the coupling 36a is that it even further reduces the likelihood of any shifting of the arch wire 10 from an optimum position. This is achieved by the holding means including the shoulders 44 of the web 13a and the adjacent shoulders 43 of the foremost portion 40 of the brace 6; these shoulders cooperate to prevent any, or any appreciable, longitudinal shifting of the web 13a relative to the brace 6. This also contributes to the likelihood that the wearer will tolerate the applicator for required intervals of time because the arch wire 10 is highly unlikely to change its position relative to the brace 6 as soon as the median portion 10a of the web 13a is snapped into the female part of the coupling 36a.

FIGS. 2 and 5 show that the lingual side or surface 47 of the brace 6 is configurated to conform to the profiles of adjacent teeth of the lower row of teeth (not shown in these Figures). This is desirable for a number of reasons, for example, because the wearer can close her or his mouth practically to the same extent as if the applicator 1 were removed from the mouth. The thickness of that portion of the brace 6 which overlies the anterior teeth need not be very pronounced, especially in the embodiment of FIGS. 4 to 6 wherein the coupling 36a is located in front of the incisors; therefore, the brace 6 permits the lower teeth to move very close to the upper teeth. It has been found that such configuration of the brace 6 is preferred by many wearers, at least during certain periods of use of the improved applicator.

Figure 8:
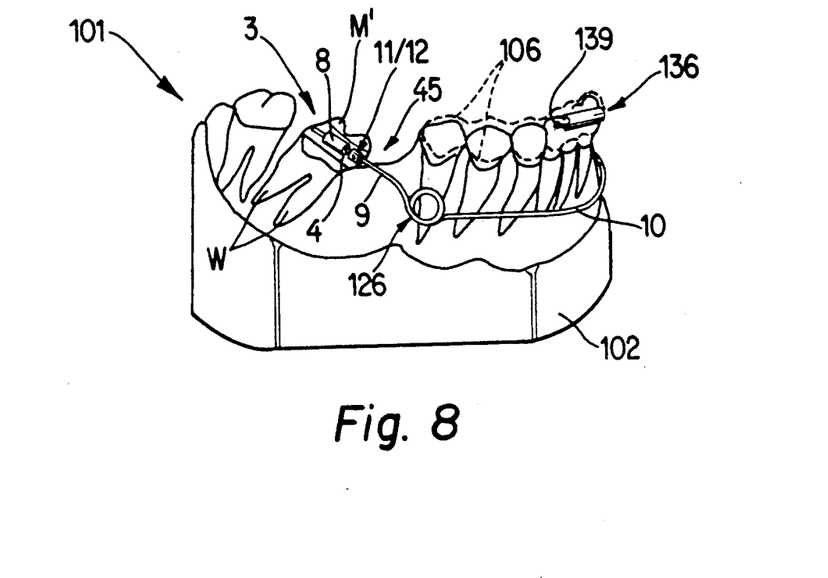
FIG. 8 is a fragmentary perspective view of a model of a lower jaw and of an applicator of directional force to a misoriented molar behind a gap in the lower row of teeth, the first component of the biasing means being uncoupled from the brace which overlies the anterior teeth of the lower row of teeth.
Figure 9:
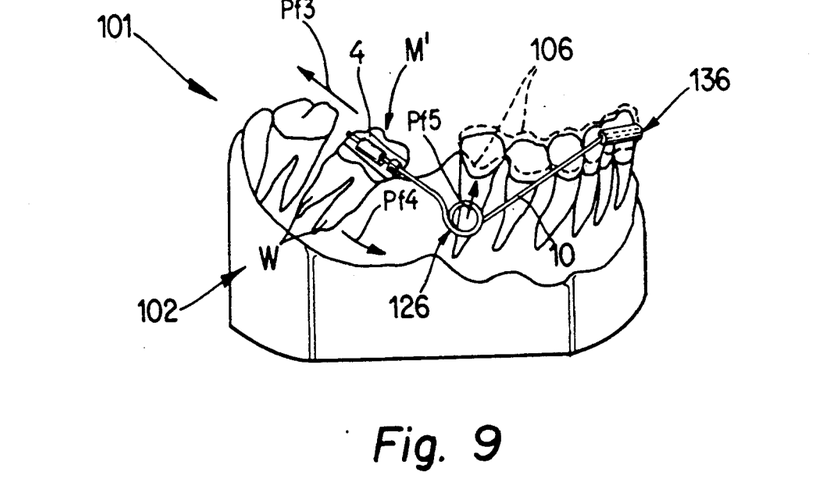
FIG. 9 shows the structure of FIG. 8 but with the first component of the biasing means properly coupled to the brace.

FIGS. 8 and 9 show an applicator 101 on a model 102 of the lower jaw. The purpose of the applicator 101 is to change the orientation of a forwardly inclined molar M' which is located immediately behind a gap 45. Such gap exists due to the absence of the foremost molar (dens molares I). The brace 106 conforms to the outlines and overlies the anterior teeth of the lower row of teeth, for example, all of the incisors, both canines and all of the bicuspids. The construction of the biasing device including the arch wire 10 is or can be identical to that of the biasing device 5 shown in FIGS. 4 to 6, i.e., the coupling 136 is located in front of the major part of the brace 106 and its slot 139 is positioned to permit the median portion of the web of the wire 10 to enter the socket of the coupling 136 from above, i.e., in a direction toward the mandible. The construction of the attachment 4 and of the respective connecting unit 3 is or can be identical with that of the corresponding parts shown in FIGS. 1 to 3. The directional force is selected in such a way that it tends to move the crown of the misoriented molar M' in the direction of arrow Pf3 while, at the same time, tending to move the roots W of the molar M' in the direction of arrow Pf4. If the resilient element 16 (not specifically shown in FIGS. 8 and 9) is omitted, the directional force is generated exclusively by the resilient component or components 126 forming integral parts of the arch wire 10. When the median portion of the web of the arch wire 10 is properly received in the socket of the coupling 136, the resilient component or components 126 preferably also generate a force in the direction of arrow Pf5. The arch wire 10 preferably comprises two resilient components 126, one at each side of the coupling 136.

It has been found that, when the crown of a forwardly inclined molar M' is to be moved rearwardly (arrow Pf3), this invariably entails at least some forward movement (arrow Pf4) of the root or roots W of such tooth. The applicator 101 preferably also includes two attachments 4 and two connecting units 3, one for the illustrated molar M' and the other for the corresponding molar at the other side of the illustrated lower row of teeth. The resilient components 126 are compelled to store energy in automatic response to movement of the web of the arch wire 10 from the position of FIG. 8 (coupling 136 disengaged) to the operative position of FIG. 9 in which the coupling 136 is engaged and the molar M' is acted upon by a force urging its crown in the direction of arrow Pf3. The component of force acting in the direction of arrow Pf5 causes the generation of force in the direction of arrow Pf3, i.e., in a direction to reduce the inclination of the tooth M' and to move its roots W toward the nearest tooth in front of it.

The applicator 101 will be equipped with additional resilient elements (corresponding to the resilient elements 16 in the applicators 1) if the orthodontist wishes to ensure that the molar M' will change its inclination (by moving the crown in the direction of arrow Pf3) while the distance of the molar M' from the immediately preceding tooth of the lower row of teeth remains unchanged. The resilient elements 16 and/or their equivalents then act in the longitudinal direction of the legs 9 of the arch wire 10 to ensure that the width of the gap 45 remains at least substantially unchanged.

The illustrated applicator 1 or 101 is susceptible of many additional modifications without departing from the spirit of the invention. For example, a deep-drawn brace 6 or 106 can be replaced with a brace wherein a plastic carrier supports several tooth-engaging connectors which can receive the adjacent anterior teeth when such brace is properly installed in the mouth of a wearer to overlie the anterior teeth of the upper or lower row of teeth. Deep-drawn plastic braces are preferred at this time because they can be produced at a reasonable cost and in available machines in contrast to a carrier-type brace which is normally produced in the laboratory at a much higher cost.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. An intraoral orthodontic applicator of directional force to one or more first teeth of the upper or lower row of teeth, particularly to one or more posterior teeth, comprising at least one attachment connectable with a first tooth; at least one brace at least partially conforming to and arranged to overlie several second teeth of the respective row; and means for biasing said at least one attachment in a selected direction, including at least one first component reacting against said at least one brace, at least one second component bearing against said at least one attachment and means for separably connecting said at least one attachment to said at least one second component, said connecting means comprising a female element and an elongated male element receivable in said female element, one of said elements being provided on said at least one attachment and the other of said elements being provided on said at least one second component, said connecting means further comprising at least one resilient element interposed between said male and female elements and a stop provided on said male element, said resilient means being interposed between said female element and said stop and said stop being movable longitudinally of said male element, said connecting means further comprising means for separably affixing said stop to said male element.

2. The applicator of claim 1, wherein said at least one attachment is connectable with a molar or a bicuspid and said at least one brace is arranged to overlie at least two anterior teeth.

3. The applicator of claim 1, wherein said at least one brace includes an integral extension arranged to conform to and overlie the jaw at the lingual side of the respective row of teeth.

4. The applicator of claim 1, wherein said at least one brace conforms to the anterior teeth of the respective row of teeth.

5. The applicator of claim 4, wherein the anterior teeth to which said brace conforms include all bicuspids, all incisors and both canines of the respective row of teeth.

6. The applicator of claim 1, wherein said brace contains a plastic material.

7. The applicator of claim 1, wherein said brace consists of deep-drawn plastic material.

8. The applicator of claim 1, wherein said brace includes a plastic carrier and connectors supported by said carrier and arranged to engage several second teeth of the respective row of teeth.

9. The applicator of claim 1, wherein said at least one attachment comprises a collar arranged to surround a first tooth.

10. The applicator of claim 1, further comprising means for separably coupling said at least one first component to said brace, said connecting means being disposed at the level or cranially of said coupling means when said at least one attachment is connected to a first tooth and said brace overlies several second teeth of the respective row of teeth.

11. The applicator of claim 1, wherein said biasing means further comprises means for separably coupling said at least one first component to said brace, said coupling means comprising a wire forming part of said first component and a socket provided in said brace and removably receiving said wire, said socket being located in the region of incisors when said brace overlies several second teeth of the respective row of teeth.

12. The applicator of claim 1, wherein said biasing means includes a springy wire including a web forming part of said first component and two legs, one of said legs forming part of said at least one second component.

13. The applicator of claim 1, further comprising means for separably coupling said first component to said brace, said coupling means including an elongated wire forming part of said first component, a socket provided in said brace and removably receiving said wire, and means for holding said wire against longitudinal movement in said socket.

14. The applicator of claim 13, wherein said holding means includes shoulders provided on said wire and flanking said socket.

15. The applicator of claim 1, wherein said brace has an exposed surface conforming to the profiles of adjacent teeth of the row of teeth confronting the row including the first tooth and the second teeth.

16. The applicator of claim 1, wherein said resilient element surround said at least one second component.

17. An intraoral orthodontic applicator of directional force to one or more first teeth of the upper or lower row of teeth, particularly to one or more posterior teeth, comprising at least one attachment connectable with a first tooth; at least one brace at least partially conforming to and arranged to overlie several second teeth of the respective row; means for biasing said at least one attachment in a selected direction, including at least one first component reacting against said at least one brace and at least one second component bearing against said at least one attachment, said biasing means comprising a substantially U-shaped springy wire including a web forming part of said at least one first component and two legs, one of said legs forming part of said at least one second component and being separably connected with said attachment; and detent means providing a separable snap-in connection between said web and said brace.

18. The applicator of claim 17, wherein said at least one attachment carries a sleeve and said biasing means includes a wire having a first portion forming part of said first component and a second portion forming part of said second component and including a tip receivable in said sleeve, said biasing means further comprising at least one resilient element reacting agianst said second portion of said wire and bearing against said sleeve to thereby bias said attachment in said selected direction.

19. The applicator of claim 18, wherein said resilient element surrounds the second portion of said wire.

20. An intraoral orthodontic applicator of directional force to one or more first teeth of the upper or lower row of teeth, particularly to one or more posterior teeth, comprising at least one attachment connectable with a first tooth; at least one brace at least partially conforming to and arranged to overlie several second teeth of the respective row; means for biasing said at least one attachment in a selected direction, including at least one first component reacting against said at least one brace and at least one second component bearing against said at least one attachment, said biasing means comprising a substantially C-shaped springy wire including a web forming part of said at least one first component and two legs, one of said legs forming part of said at least one second component and being separably connected with said attachment; and detent means providing a separable snap-in connection between said web and said brace.

21. An intraoral orthodontic applicator of directional force to one or more first teeth of the upper or lower row of teeth, particularly to one or more posterior teeth, comprising at least one attachment connectable with a first tooth; at least one brace at least partially conforming to and arranged to overlie several second teeth of the respective row; means for biasing said at least one attachment in a selected direction, including at least one first component reacting against said at least one brace and at least one second component bearing against said at least one attachment; and means for separably coupling said first component to said at least one brace, said coupling means comprising a length of wire forming part of said at least one first component and a socket provided in said at least one brace, said wire being received in said socket with snap action, said at least one brace having a labial side and said socket being provided in the labial side of said at least one brace and being located in the region of the incisors when said at least one brace overlies several second teeth of the respective row of teeth.

22. The applicator of claim 21, wherein said biasing means further comprises means for separably connecting said at least one attachment to said at least one second component.

23. The applicator of claim 22, wherein said connecting means includes a female element and a male element receivable in said female element, one of said elements being provided on said at least one attachment and the other of said elements being provided on or constituting said at least one second component.

24. The applicator of claim 22, wherein said connecting means comprises a sleeve provided on said at least one attachment and extending in substantial parallelism with the adjacent portion of the respective row of teeth when said at least one attachment is connected to a first tooth, and a plug provided on said at least one second component and receivable in said sleeve.

25. The applicator of claim 22, wherein said connecting means comprises a female element and a male element receivable in said female element, one of said elements being provided on said at least one attachment and the other of said elements being provided on said at least one second component, said connecting means further comprising at least one resilient element interposed between said male and female elements.

26. The applicator of claim 25, wherein said connecting means further comprises a stop provided on said male element and said resilient means is interposed between said female element and said stop.

27. The applicator of claim 21, wherein said biasing means further comprises at least one resilient component operating between said first and second components to bias said brace toward the roots of the second teeth.

28. The applicator of claim 27, wherein said biasing means comprises a springy wire including a first portion forming part of said first component, a second portion forming part of said second component and a third portion forming part of or constituting said resilient component.

29. The applicator of claim 28, wherein said third portion of said wire includes at least one convolution.

30. The applicator of claim 21 for applying directional force to an inclined molar forming part of the lower row of teeth and being separated by a gap from the nearest anterior tooth, wherein said biasing means comprises a resilient component disposed between said first and second components to apply to said at least one attachment a force in a direction to upright the inclined molar.

31. The applicator of claim 30, wherein said second component includes an elongated piece of wire separably connected with said at least one attachment, and an elastic element operating between said wire and said at least one attachment in the longitudinal direction of the wire.

32. The applicator of claim 21, wherein said biasing means further comprises a resilient element which surrounds said second component.

* * * * *